US006214366B1

(12) United States Patent
Prusiner et al.

(10) Patent No.: US 6,214,366 B1
(45) Date of Patent: *Apr. 10, 2001

(54) CLEARANCE AND INHIBITION OF CONFORMATIONALLY ALTERED PROTEINS

(75) Inventors: Stanley B. Prusiner; Surachai Supattapone; Michael Scott, all of San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/322,903

(22) Filed: Jun. 1, 1999

(51) Int. Cl.$^7$ .................................................. A01N 25/10
(52) U.S. Cl. ......................... 424/405; 424/438; 424/442; 424/484; 424/DIG. 16; 424/78.32; 424/78.35; 424/78.36; 424/78.37; 424/78.38; 514/772.3; 514/772.4; 514/772.5; 514/772.6; 514/772.7
(58) Field of Search ............................. 424/78.32, 78.35, 424/78.38, 405, 438, 442, DIG. 16; 514/772.3–772.7

(56) References Cited

U.S. PATENT DOCUMENTS

| 4,587,329 | 5/1986 | Tomalia et al. . |
| 5,499,979 | 3/1996 | Wong et al. . |
| 5,834,020 | * 11/1998 | Margerum et al. . |
| 5,919,442 | * 7/1999 | Yin et al. ........................... 424/78.18 |

OTHER PUBLICATIONS

Basler et al., "Scrapie and Cellular PrP Isoforms Are Encoded by the Same Chromosomal Gene," *Cell*, (Aug. 1, 1986, 46:417–28).
Combs et al, "Identification of Microglial Signal Transduction Pathways Mediating a Neruotoxic Response to Amyloidogenic Fragments of β–Amyloid and Prion Proteins," *The Journal of Neuroscience*, (Feb. 1, 1999) 19(3):928–939.
Gajdusek, "Unconventional Viruses and the Origin and Disappearance of Kuru" *Science* (Sep. 2, 1977), 197(4307):943–960.
Glenner et al., "Amyloidosis of the nervous system" *J. Neurol. Sci.* (1989) 94:1–28.
Haan et al. "Amyloid in Central Nervous System Disease," *Clin. Neurol Neurosurg.* (1990) 92(4):305–310.
Hardy, "Amyloid, the Presenilins and Alzheimer's Disease," *Trends Neurosci.* (1997) 20(4):154–159.
Kalaria et al., Differential Degeneration of the Cerebral Microvasculature in Alzheimer's Disease *NeuroReport* (1995) 6:477–480.
Kawai et al. "Degeneration of Vascular Muscle Cells in Cerebral Amyloid Angiopathy of Alzheimer's Disease." *Brain Res*, (1993). 623:142–146.
Kelly, "Alternative Conformations of Amyloidogenic Proteins Govern Their Behavior," *Current Opinions in Structural Biology*, (1996) Strut Biol 6(1):11–17.

Lai, et al., "The Acid–Mediated Denaturation Pathway of Transthyretin Yields a Conformational Intermediate Than Can Self–Assemble into any Amyloid," *Biochemistry*, (1996), 35(20):6470–6482.

Lendon et al., "Exploring the Etiology of Alzheimer Disease Using Molecular Genetics," *J. Am. Med. Assoc.*, (1997), 277(10):825–831.

Mandybur, "Cerebral Anyloid Angiopathy and Astroc Glisos in Alzheimer's Disease," *Acta Neuropath.*, (1989) 78:329–331.

Martin et al., "Synaptic Pathology and Glial Responses to Neuronal Injury Precede the Formation of Senile Plaques and Amyloid Deposits in the Aging Cerebral Cortex," *Amer. Journal of Pathology*, (1994) 145(6):1358–1381.

Masliah et al., "Comparison of Neurodegenerative Pathology in Transgenic Mice Overexpressing V717F β–Amyloid Precursor Protein and Alzheimer's Disease," *Journal of Neuroscience*, (Sep. 1996) 16(18):5795–5811.

Medori et al., Fatal Familial Insomnia, A Prion Disease With a Mutation at Codon 178 of The Prion Protein Gene, *New England Journal of Medicine*, (Feb. 13, 1992), 326(7):444–449.

McCutchen, et al., "Transthyretin Mutation Leu–55–Pro Significantly Alters Tetramer Stability and Increases Amyloidogenicity," *Biochemistry*, (1993) 32(45):12119–12127.

McCutchen, et al.., "Intermolecular Disulfide Linkages Are Not Required for Transthyretin Amyloid Fibril Formation in Vitro," *Biochem., Biophys, Res. Commun*, (1993) 197(2) 415–21.

Miroy, "Inhibiting Transthyretin Amyloid Fibril Formation via Protein Stabilization," *Proc. Natl. Acad. Sci. USA*, (Dec. 1996), 93(26):15051–15056.

Pan, et al., "Conversion of α–Helices into β–Sheets Features in the Formation of the Scrapie Prion Proteins," *Proc. Natl. Acad. Sci. USA*, (1993), 90:10962–10966.

Prusiner, "Biology of Prions," *The Molecular and Genetic Basis of Neurological Disease*, 2nd Edition, Ch. 7., (1997), pp. 103–143.

(List continued on next page.)

Primary Examiner—Neil S. Levy
(74) *Attorney, Agent, or Firm*—Dianna L. DeVore; Bozicevic, Field and Francis LLP

(57) ABSTRACT

The present invention provides a method of arresting, preventing and/or reversing the impairment of central and peripheral nervous system function comprising reducing insoluble protein deposit burden by the administration of branched polycationic compounds and pharmaceutical compositions containing such branched polycationic compounds. The compounds used in the preferred method of the invention are branched dendritic polycations.

14 Claims, No Drawings

OTHER PUBLICATIONS

Safar, et al., "Conformational Transitions, Dissociation, and Unfolding of Scrapie Amyloid (Prion) Protein," *Journal of Biol. Chem.*, (1993) 268(27):20276–20284.

Selkoe et al., "β–Amyloid Precursor Protein of Alzheimer Disease Occurs as 110–to 135–Kilodalton Membranes–Assoicated Proteins in Neural and Nonneural Tissues," *Proc. Natl. Acad. Sci. USA*. (1988) 85:7341–7345.

Selkoe, "Physiological Production of the β–Amyloid Protein and the Mechanism of Alzheimer's Disease," *Trends in Neurosciences*, (1993) 16(10):403–409.

Selkoe, "Amyloid β–Protein and the Genetics of Alzheimer's Disease," *Journ. of Biol. Chem.*, (1996), 271(31):18295–8.

Wilesmith, et al., "Bovine Spongiform Encephalopathy," *Current Topics in Microbiology and Immunolog*, (1991) 172:21–38.

Yankner, "New Clues to Alzheimer's Disease: Unraveling the Roles of Amyloid and Tau," *Nature Medicine*, (1996) 2(8):850–852.

* cited by examiner-

CLEARANCE AND INHIBITION OF CONFORMATIONALLY ALTERED PROTEINS

FIELD OF THE INVENTION

The present invention is related generally to compounds for the treatment of degenerative diseases and to methods of use of such compounds.

BACKGROUND OF THE INVENTION

The assembly and misassembly of normally soluble proteins into conformationally altered proteins is thought to be a causative process in a variety of diseases including the prion diseases, the amyloidoses, and other common degenerative diseases. Structural conformational changes are required for the conversion of a normally soluble and functional protein into a defined, insoluble state. Examples of such insoluble protein include: Aβ peptide in amyloid plaques of Alzheimer's disease and cerebral amyloid angiopathy (CAA); α-synuclein deposits in Lewy bodies of Parkinson's disease, Tau in neurofibrillary tangles in frontal temporal dementia and Pick's disease; superoxide dismutase in amyotrophic lateral sclerosis; huntingtin in Huntington's disease; and prions in Creutzfeldt-Jakob disease (CJD): (for reviews, see Glenmer et al. (1989) *J. Neurol. Sci.* 94:1–28; Haan et al. (1990) *Clin. Neurol. Neurosurg.* 92(4):305–310). Often these highly insoluble proteins form aggregates composed of nonbranching, fibrillar proteins with the common characteristic of a β-pleated sheet conformation. In the CNS, amyloid can be present in cerebral and meningeal blood vessels (cerebrovascular deposits) and in brain parenchyma (plaques). Neuropathological studies in human and animal models indicate that cells proximal to amyloid deposits are disturbed in their normal functions (Mandybur (1989) *Acta Neuropathol.* 78:329–331; Kawai et al. (1993) *Brain Res.* 623:142–6; Martin et al. (1994) *Am. J. Pathol.* 145:1348–1381; Kalaria et al. (1995) *Neuroreport* 6:477–80; Masliah et al. (1996)*J. Neurosci.* 16:5795–5811). Other studies additionally indicate that amyloid fibrils may actually initiate neurodegeneration (Lendon et al. (1997) *J. Am. Med Assoc.* 277:825–3 1; Yankner (1996) *Nat. Med.* 2:850–2; Selkoe (1996) *J. Biol. Chem.* 271:18295–8; Hardy (1997) *Trends Neurosci.* 20:154–9).

The PrP gene of mammals expresses a protein which can be the soluble, non-disease form $PrP^C$ or be converted to the insoluble, disease form $PrP^{Sc}$. $PrP^C$ is encoded by a single-copy host gene [Basler, Oesch et al. (1986) *Cell* 46:417–428] and when $PrP^C$ is expressed it is generally found on the outer surface of neurons. Many lines of evidence indicate that prion diseases result from the transformation of the normal form of prion protein ($PrP^C$) into the abnormal form ($PrP^{Sc}$). There is no detectable difference in the amino acid sequence of the two forms. However, $PrP^{Sc}$ when compared with $PrP^C$ has a conformation with higher β-sheet and lower α-helix content (Pan, Baldwin et al. (1993) *Proc Natl Acad Sci USA* 90:10962–10966; Safar, Roller et al. (1993) *J Biol Chem* 268:20276–20284). The presence of the abnormal $PrP^{Sc}$ form in the brains of infected humans or animals is the only disease-specific diagnostic marker of prion diseases.

$PrP^{Sc}$ plays a key role in both transmission and pathogenesis of prion diseases (spongiforn encephalopathies) and it is a critical factor in neuronal degeneration (Prusiner (1997) The Molecular and Genetic Basis of Neurological Disease, 2nd Edition: 103–143). The i most common prion diseases in animals are scrapie of sheep and goats and bovine spongiform encephalopathy (BSE) of cattle (Wilesmith and Wells (1991) *Curr Top Microbiol Immunol* 172:21–38). Four prion diseases of humans have been identified: (1) kuru, (2) Creutzfeldt-Jakob Disease (CJD), (3) Gerstmann-Sträussler-Sheinker Disease (GSS), and (4) fatal familial insomnia (FFI) [Gajdusek (1977) *Science* 197:943–960; Medori Tritschler et al. (1992) *N Engl J Med* 326:444–449]. Initially, the presentation of the inherited human prion diseases posed a conundrum which has since been explained by the cellular genetic origin of PrP.

In both AD and CAA, the main amyloid component is the arnyloid β protein (Aβ).

The Aβ peptide, which is generated from the amyloid β precursor protein (APP) by two putative secretases, is present at low levels in the normal CNS and blood. Two major variants, $Aβ_{1-40}$ and $Aβ_{1-42}$, are produced by alternative carboxy-terminal truncation of APP (Selkoe et al.(1988) *Proc. Natl. Acad. Sci. USA* 85:7341–7345; Selkoe, (1993) *Trends Neurosci* 16:403–409). $Aβ_{1-42}$ is the more fibrillogenic and more abundant of the two peptides in amyloid deposits of both AD and CAA. In addition to the amyloid deposits in AD cases described above, most AD cases are also associated with amyloid deposition in the vascular walls (Hardy (1997), supra; Haan et al. (1990), supra; Terry et al., supra; Vinters (1987), supra; Itoh et al. (1993), supra; Yamada et al. (1993), supra; Greenberg et al. (1993), supra; Levy et al. (1990), supra). These vascular lesions are the hallmark of CAA, which can exist in the absence of AD.

Human transthyretin (TTR) is a normal plasma protein composed of four identical, predominantly β-sheet structured units, and serves as a transporter of hormone thyroxin. Abnormal self assembly of TTR into amyloid fibrils causes two forms of human diseases, namely senile systemic amyloidosis (SSA) and familial amyloid polyneuropathy (FAP) (Kelly (1996) *Curr Opin Strut Biol* 6(1):11–7). The cause of amyloid formation in FAP are point mutations in the TTR gene; the cause of SSA is unknown. The clinical diagnosis is established histologically by detecting deposits of amyloid in situ in bioptic material.

To date, little is known about the mechanism of TTR conversion into amyloid in vivo. However, several laboratories have demonstrated that amyloid conversion may be simulated in vitro by partial denaturation of normal human TTR [McCutchen, Colon et al. (1993) *Biochemistry* 32(45):12119–27; McCutchen and Kelly (1993) *Biochem Biophys Res Commun* 197(2) 415–21]. The mechanism of conformational transition involves monomeric conformational intermediate which polymerizes into linear β-sheet structured amyloid fibrils [Lai, Colon et al. (1996) *Biochemistry* 35(20):6470–82]. The process can be mitigated by binding with stabilizing molecules such as thyroxin or triiodophenol (Miroy, Lai et al. (1996) *Proc Natl Acad Sci USA* 93(26):15051–6).

The precise mechanisms by which neuritic plaques are formed and the relationship of plaque formation to the disease-associated neurodegenerative processes are not well-defined. The amyloid fibrils in the brains of Alzheimer's and prion disease patients are known to result in the inflammatory activation of certain cells. For example, primary microglial cultures and the THP-1 monocytic cell line are stimulated by fibrillar β-amyloid and prion peptides to activate identical tyrosine kinase-dependent inflammatory signal transduction cascades. The signaling response elicited by β-amyloid and prion fibrils leads to the production of neurotoxic products, which are in part responsible for the neurodegenerative. C. K. Combs et al,*J Neurosci* 19:928–39 (1999).

In view of the above points, there is clearly a need for a method of clearing and/or preventing the formation of insoluble protein deposits associated with diseases such as Alzheimer's disease and prion-mediated disorders. Such a method would be effective in the treatment, prevention, and perhaps reversal of the neurological decline found in patients suffering from such disorders.

SUMMARY OF THE INVENTION

The present invention provides methods of arresting, preventing and/or reversing the impairment of physiologic systems, the methods comprising reducing the burden of insoluble protein deposits by the administration of branched polycationic agents or pharmaceutical compositions containing such branched polycationic agents. The agents used in the preferred method of the invention are highly-branched polycations, e.g. dendritic polycations.

In one embodiment, the invention provides pharmaceutical compositions for the treatment of protein deposit formation in an animal which compositions contain branched polycations agents, preferably highly-branched polycations. Branched polycations for use in the invention include, but are not limited to, polypropylene imine, polyethyleneimine (PEI) poly(4'-aza-4'-methylheptamethylene D-glucaramide), polyamidoamines and suitable fragments and/or variants of these compounds. The pharmaceutical compositions can also contain other active ingredients, either separate or complexed to the branched polycations. Exemplary active agents include pharmaceutical agents to further reduce or prevent insoluble protein deposit (e.g. modulators of apoE expression for reduction of β-amyloid plaques in AD), analgesic agents, antimicrobial agents, anti-inflammatory agents, antioncogenic agents, and antiviral agents.

The invention also provides methods for reducing the burden of insoluble protein deposits in various host tissues by administering a highly-branched polycationic agent to the host. Preferably the highly-branched polycation is administered over a period of time, either continuously or in multiple dosage units. The animal treated may be suffering from any degenerative disorder associated with insoluble protein deposits. For example, the animal may be a human suffering from Alzheimer's Disease or a cow suffering from BSE.

The invention also features a method for reversing protein deposits in degenerative diseases of a subject by administration of a polycationic compound. The compound is preferably a highly-branched polycation, and the subject may be suffering from degenerative disorder.

The invention also features a method for preventing the formation of protein deposits in animals or humans at risk for a degenerative disease by administration of a highly-branched polycationic compound in an amount sufficient to suppress formation of the protein deposits. The compound used in this method is preferably a highly-branched polycation. Subjects for treatment with this method may be genetically predisposed to developing degenerative disease, such as humans genetically at risk for AD, Parkinsonds disease, ALS, FTD, Pick's disease, Huntington's disease or CJD. Subjects may also be determined to be at risk due to exposure to infectious agents causing amyloid-associated disorders, e.g cattle exposed to bovine prions from a BSE contaminated source.

A feature of the compounds of the present invention is their ability to mediate the clearance of $PrP^{Sc}$ from cultured cells under non-cytotoxic conditions.

An advantage of the pharmaceutical compositions of the invention is that the highly-branched polycation administered is non-toxic to the mammalian host at a dosage of 0.001 mg to 1 mg/kg body weight per day.

Another advantage is that subjects treated with the methods of invention remain free of insoluble protein deposits after clearance.

These and other objects, advantages, and features of the invention will become apparent to those persons skilled in the art upon reading the details of the compounds, and assay method more fully described below.

DETAILED DESCRIPTION OF PREFERRED EMBODIMENTS

Before the present compounds and methods of use are described, it is to be understood that this invention is not limited to particular compounds, modes of administration and the like described and, as such, may of course vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The terms "treatment", "treating", "treat" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in an animal, particularly a human, and includes:

(a) preventing the disease or symptom from occurring in a subject which may be predisposed to the disease or symptom but has not yet been diagnosed as having it;

(b) inhibiting the disease of its symptom, i.e., arresting development of the disease or its symptoms; or (c) relieving the disease symptom, i.e., causing regression of the disease or symptom.

By "effective dose" or "amount effective" is meant an administration of a compound sufficient to provide the desired physiological and/or psychological change. This will vary depending on the patient, the disease and the treatment. The dose may either be a therapeutic dose, in which case it should sufficiently alter levels of insoluble protein deposits in the subject to alleviate or ameliorate the symptoms of the disorder or condition, or a prophylactic dose, which should be sufficient to prevent accumulation of insoluble protein deposits to an undesirable level.

The term "compound" as used herein describes any molecule, e.g. protein or small molecule pharmaceutical, with the capability of affecting the molecular and clinical phenomena associated with amyloid-associated disorders, and particularly AD, CAA, and prion-mediated disorders.

The term "diagnosis" is used herein to cover any type of analysis used to determine or project a status which includes identification of a disease from its symptoms and determining the presence of molecules associated with a disorder (e.g., $PrP^{Sc}$ for CJD, increased apoE levels for AD) in an area (e.g., brain tissue) which suggest a disease status.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The term "$LD_{50}$" as used herein is the dose of an active substance that will result in 50 percent lethality in all treated experimental animals. Although this usually refers to invasive administration, such as oral, parenteral, and the like, it may also apply to toxicity using less invasive methods of administration, such as topical applications of the active substance.

The term "amine-terminated" includes primary, secondary and tertiary amines.

The terms "PrP protein", "PrP" and like are used interchangeably herein and shall mean both the infectious particle form $PrP^{Sc}$ known to cause diseases (spongiform encephalopathies) in humans and animals and the noninfectious form $PrP^{C}$ which, under appropriate conditions is converted to the infectious $PrP^{Sc}$ form.

The terms "prion", "prion protein", "$PrP^{Sc}$ protein" and the like are used interchangeably herein to refer to the infectious $PrP^{Sc}$ form of a PrP protein, and is a contraction of the words "protein" and "infection." Particles are comprised largely, if not exclusively, of $PrP^{Sc}$ molecules encoded by a PrP gene. Prions are distinct from bacteria, viruses and viroids. Known prions infect animals to cause scrapie, a transmissible, degenerative disease of the nervous system of sheep and goats, as well as bovine spongiform encephalopathy (BSE), or "mad cow disease", and feline spongiform encephalopathy of cats. Four prion diseases known to affect humans are (1) kuru, (2) Creutzfeldt-Jakob Disease (CJD), (3) Gerstmann-Straiussler-Scheinker Disease (GSS), and (4) fatal familial insomnia (FFI). As used herein "prion" includes all forms of prions causing all or any of these diseases or others in any animals used - and in particular in humans and domesticated farm animals.

The term "PrP gene" is used herein to describe genetic material which expresses proteins including known polymorphisms and pathogenic mutations. The term "PrP gene" refers generally to any gene of any species which encodes any form of a prion protein. Some commonly known PrP sequences are described in Gabriel et al., *Proc. Natl. Acad. Sci. USA* 89:9097–9101 (1992) and U.S. Pat. No. 5,565,186, incorporated herein by reference to disclose and describe such sequences. The PrP gene can be from any animal, including the "host" and "test" animals described herein and any and all polymorphisms and mutations thereof, it being recognized that the terms include other such PrP genes that are yet to be discovered. The protein expressed by such a gene can assume either a $PrP^{C}$ (non-disease) or $PrP^{Sc}$ (disease) form.

The terms "standardized prion preparation", "prion preparation", "preparation" and the like are used interchangeably herein to describe a composition obtained from the brain tissue of mammals which exhibits signs of prion disease: the mammal either (1) include a transgene as described herein; (2) have and ablated endogenous prion protein gene; (3) have a high number of prion protein gene from a genetically diverse species; or (4) are hybrids with an ablated endogenous prion protein gene and a prion protein gene from a genetically diverse species.

Different combinations of 1–4 are possible, e.g., 1 and 2. The mammals from which standardized prion preparations are obtained exhibit clinical signs of CNS dysfunction as a result of inoculation with prions and/or due to developing the disease of their genetically modified make up, e.g., high copy number of prion protein genes.

The term "Alzheimer's disease" (abbreviated herein as "AD") as used herein refers to a condition associated with formation of neuritic plaques comprising arnyloid P protein, primarily in the hippocampus and cerebral cortex, as well as impairment in both learning and memory. "AD" as used herein is meant to encompass both AD as well as AD-type pathologies.

The term "AD-type pathology" as used herein refers to a combination of CNS alterations including, but not limited to, formation of neuritic plaques containing amyloid , protein in the hippocampus and cerebral cortex. Such AD-type pathologies can include, but are not necessarily limited to, disorders associated with aberrant expression and/or deposition of APP, overexpression of APP, expression of aberrant APP gene products, and other phenomena associated with AD. Exemplary AD-type pathologies include, but are not necessarily limited to, AD-type pathologies associated with Down's syndrome that is associated with overexpression of APP.

The term "phenomenon associated with Alzheimer's disease" as used herein refers to a structural, molecular, or functional event associated with AD, particularly such an event that is readily assessable in an animal model. Such events include, but are not limited to, amyloid deposition, neuropathological developments, learning and memory deficits, and other AD-associated characteristics.

The term "cerebral arnyloid angiopathy" (abbreviated herein as CAA) as used herein refers to a condition associated with formation of amyloid deposition within cerebral vessels which can be complicated by cerebral parenchymal hemorrhage. CAA is also associated with increased risk of stroke as well as development of cerebellar and subarachnoid hemorrhages (Vinters (1987) *Stroke* 18:311–324; Haan et al. (1994) *Dementia* 5:210–213; Itoh et al. (1993) *J. Neurol. Sci.* 116:135–414). CAA can also be associated with dementia prior to onset of hemorrhages. The vascular amyloid deposits associated with CAA can exist in the absence of AD, but are more frequently associated with AD.

The term "phenomenon associated with cerebral arnyloid angiopathy" as used herein refers to a molecular, structural, or functional event associated with CAA, particularly such an event that is readily assessable in an animal model. Such events include, but are not limited to, amyloid deposition, cerebral parenchymal hemorrhage, and other CAA-associated characteristics.

The term "β-amyloid deposit" as used herein refers to a deposit in the brain composed of Aβ as well as other substances. Abbreviations used herein include:

CNS for central nervous system;
BSE for bovine spongiform encephalopathy;
CJD for Creutzfeldt-Jacob Disease;
FFI for fatal familial insomnia;
GSS for Gerstmann-Straussler-Scheinker Disease;
AD for Alzheimer's disease;
CAA for cerebral amyloid angiopathy;
Hu for human;
HuPrP for human prion protein;
Mo for mouse;
MoPrP for mouse prion protein;
SHa for a Syrian hamster;
SHaPrP for a Syrian hamster prion protein;
$PrP^{Sc}$ for the scrapie isoform of the prion protein;
$PrP^{C}$ for the cellular contained common, normal isoform of the prion protein;
PrP 27–30 or $PrP^{Sc}$ 27–30 for the treatment or protease resistant form of $PrP^{Sc}$;
$MoPrP^{Sc}$ for the scrapie isoform of the mouse prion protein;
N2a for an established neuroblastoma cell line used in the present studies;
ScN2a for a chronically scrapie-infected neuroblastoma cell line;
ALS for amyotrophic lateral sclerosis;
HD for Huntington's disease;
FTD for frontotemporal dementia;
SOD for superoxide dismutase

GENERAL ASPECTS OF THE INVENTION

The invention is based on the discovery that several dendritic polycations, including the starburst dendrimers Superfect™ (QIAGEN®, Valencia, Calif.), polyamidoamide (PAMAM), and the hyperbranched polycation polyethyleneimine (PEI), were surprisingly found to eliminate $PrP^{Sc}$ from cultured scrapie-infected neuroblastoma cells. These highly-branched, polycationic compounds provide a novel class of therapeutic agents to combat prion diseases and other amyloidoses. The removal of $PrP^{Sc}$ is dependent on both the concentration of dendritic polymer and length of exposure. Dendritic polymers were able to clear $PrP^{Sc}$ at concentrations which were not cytotoxic. Repeated exposures to heat-degraded starburst PAMAM dendrimer or PEI caused a dramatic reduction in $PrP^{Sc}$ levels which persisted for a month even after removal of the compound. Dendritic polycations did not appear to destroy purified $PrP^{Sc}$ in vitro, and therefore may act through a generalized mechanism. Dendritic polycations represent a class of compounds which may become novel therapeutic agents in prion diseases and other disorders involving insoluble protein deposits, such as the amyloidoses.

Cationic lipids, such as DOTAP cationic lipids (Boehringer Mannheim, Indianapolis, Ind.), are routinely used to transfect cells with plasmid DNA. As part of an effort to identify a more efficient method for transfecting ScN2a cells, alternative protocols were evaluated including those using dendritic compounds. An unexpected finding from these experiments was a reduction in $PrP^{Sc}$ levels in ScN2a cells incubated with specific dendritic polycations. Furthermore, when ScN2a cells were exposed to multiple doses of polycations, $PrP^{Sc}$ levels remained very low 4 weeks after removal of the compound, suggesting that the treatment protocol may have eliminated scrapie infection completely. Furthermore, preliminary experiments show that dendritic polycations are ineffective at destroying $PrP^{Sc}$ in brain homogenates and purified preparations.

Without being bound to a specific theory, the findings upon which the present invention are based could be due to the potent ability of dendritic polycations to facilitate the clearance of $PrP^{Sc}$ by rupturing endosomes. The dendritic polycations which were effective in clearing $PrP^{Sc}$ from ScN2a cells in our experiments are potent lysomotropic, osmotic agents which can swell in acidic environments and rupture endosomes (Boussif et al., (1995) Proc. Natl. Acad. Sci. USA 92:7297–7301; Haensler and Szoka, (1993) Bioconjugate Chem. 4:372–379). $PrP^{Sc}$ has been shown to reside along the endocytic pathway (Borchelt et al., (1992) J. Biol. Chem. 267:16188–16199). Therefore, dendritic polycations may clear $PrP^{Sc}$ from ScN2a cells by rupturing endosomes and exposing $PrP^{Sc}$ to cytosolic degradation processes. Alternatively, dendritic polycations might act by binding to $PrP^{Sc}$, thereby making $PrP^{Sc}$ accessible to normal cellular degradative processes.

Because these compounds may activate a generalized mechanism of clearance, these compounds are useful as potential therapeutic agents against not only prion diseases, but also against amyloidoses such as Alzheimer's disease, multiple myeloma, Type-2 diabetes, and familial amyloidotic polyneuropathy. They are also useful in treating degenerative disorders that involve the presence and/or accumulation of insoluble proteins, such as frontotemporal dementia, Parkinson's disease, Pick's disease, Huntington's disease and the like.

DISEASES ASSOCIATED WITH INSOLUBLE PROTEINS

Much of the disclosure and the specific examples provided herein relate to the use of the invention in connection with treatment of $PrP^{Sc}$. However, as indicated above, the compounds of the invention can be applied to the treatment of any disease involving a protein which assumes two or more different shapes, one of which is constricted (generally associated with the disease) and one which is relaxed (generally not a disease conformation). The following is a non-limiting list of diseases with associated proteins which assume two or more different conformation—a constricted and a relaxed conformation.

| Disease | Insoluble Proteins |
|---|---|
| Alzheimer's Disease | APP, Aβ peptide, α1-antichymotrypsin, tau, non-Aβ component |
| Prion diseases, Creutzfeld Jakob disease, scrapie and bovine spongiform encephalopathy | $PrP^{Sc}$ |
| ALS | SOD and neurofilament |
| Pick's disease | Pick body |
| Parkinson's disease | α-synuclein in Lewy bodies |
| Frontotemporal dementia | Tau in neurofibrillary tangles |
| Diabetes Type II | Amylin |
| Multiple myeloma-plasma cell dyscrasias | IgGL-chain |

-continued

| Disease | Insoluble Proteins |
|---|---|
| Familial amyloidotic polyneuropathy | Transthyretin |
| Medullary carcinoma of thyroid | Procalcitonin |
| Chronic renal failure | $\beta_2$-microglobulin |
| Congestive heart failure | Atrial natriuretic factor |
| Senile cardiac and systemic amyloidosis | Transthyretin |
| Chronic inflammation | Serum amyloid A |
| Atherosclerosis | ApoA1 |
| Familial amyloidosis | Gelsolin |
| Huntington's disease | Huntingtin |

TABLE 1

LIST OF PAMAM DENDRIMERS AND THEIR MOLECULAR WEIGHTS (Ethylene Diamine core, amine terminated).

| GENERATION | TERMINAL GROUPS | MOL. WT. g/mole |
|---|---|---|
| 0 | 4 | 517 |
| 1 | 8 | 1430 |
| 2 | 216 | 3256 |
| 3 | 32 | 6909 |
| 4 | 64 | 14,215 |
| 5 | 128 | 28,795 |
| 6 | 256 | 58,048 |
| 7 | 512 | 116,493 |
| 8 | 1024 | 233,383 |
| 9 | 2048 | 467,162 |
| 10 | 4096 | 934,720 |

DENDRIMER COMPOUNDS OF THE INVENTION

Dendrimers are branched compounds also known as "starburst" or "star" polymers due to a characteristic star-like structure. Dendrimers of the invention are polymers with structures built from $AB_n$ monomers, with $n \geq 2$, and preferably n=2 or 3. Such dendrimers are highly branched and have three distinct structural features: 1) a core, 2) multiple peripheral end-groups, and 3) branching units that link the two. Dendrimers may be cationic (full generation dendrimers) or anionic (half generation dendrimers). For a review on the general synthesis, physical properties, and applications of dendrimers, see, e.g., Tomalia et. al, Angew. Chem. Int. Ed. Engl., 29:138–175, (1990); Y. Kim and C. Zimmerman, Curr Opin Chem Biol, 2:733–7421 (1997).

In a preferred embodiment, the pharmaceutical compositions of the invention comprise a cationic dendrimer. Examples of suitable dendrimers are disclosed in U.S. Pat. Nos. 4,507,466, 4,558,120, 4,568,737, 4,587,329, 4,631, 337, 4,694,064, 4,713,975, 4,737,550, 4,871,779, and 4,857, 599 to D. A. Tomalia, et al., which are hereby incorporated by reference for disclosure of such compounds. Dendrimers typically have tertiary amines which have a pKa of 5.7. The dendrimers can optionally be chemically or heat treated to remove some of the tertiary amines. Other suitable cations include polypropylene imine, polyethyleneimine (PEI), which has tertiary amines with a pKa of 5.9, and poly(4'-aza-4'-methylheptamethylene D-glucaramide), which has tertiary amines with a pKaof6.0.

Preferably, the dendrimers for use in the invention are polyamidoamines (hereinafter "PAMAM"). PAMAM dendrimers are particularly biocompatible, since polyamidoamine groups resemble peptide bonds of proteins.

Dendrimers are prepared in tiers called generations and therefore have specific molecular weights. The full generation PAMAM dendrimers have amine terminal groups, and are cationic, whereas the half generation dendrimers are carboxyl terminated. Full generation PAMAM dendrimers are thus preferred for use in the present invention. PAMAM dendrimers may be prepared having different molecular weights and have specific values as described in Table 1 below for generations 0 through 10.

As shown in Table 1, the number of terminal amine groups for PAMAM dendrimers generations 0 through 10 range from 4 to 4,096, with molecular weights of from 517 to 934,720. PAMAM dendrimers are available commercially from Aldrich or Dendritech. Polyethyleneimine or polypropylene dendrimers or quaternized forms of amine-terminated dendrimers may be prepared as described by Tomalia et. al, Angew, Chem. Int. Ed. Engl., 29:138–175 (1990).

PHARMACEUTICAL COMPOSITION

As demonstrated in the Examples below, highly-branched polycations, e.g. dendrimer compounds, affect the extent and distribution of $PrP^{Sc}$ protein deposits in scrapie-infected cells. The presence of dendrimers at relatively low, non-cytotoxic levels results in a significant reduction in detectable $PrP^{Sc}$ in cells and brain homogenates. Thus, the present invention encompasses pharmaceutical compositions for reducing, inhibiting, or otherwise mitigating plaque formation in a subject susceptible to neuronal degenerative disorders associated with protein deposit formation.

Formulations

Pharmaceutical formulations of the invention preferably contain highly branched polycations, e.g. polycationic dendrimer, in a concentration from 0.1 to 10% of the formulation. They may also be used in appropriate association with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol. The formulations may also contain conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

For use in the subject methods, the highly-branched polycations, e.g. dendrimers, may be formulated with other pharmaceutically active agents, particularly other agents that can modulate onset or symptoms of the condition to be treated. For example, to treat Alzheimer's disease or CAA, the polycation compound can be co-administered with one or more biologically active agents that reduce protein deposit formation and/or prevent protein deposit formation. Examples of such compounds include nonsteroid anti-inflammatory drugs (NSAIDs) or aspirin-like drugs (J. R. Vane, *Semin Arthritis Rheum* 26:2–10 (1997)), selective inhibitors of COX-2 (J. R. Vane *Int J Tissue React*, 20:3–15 (1998)), protein phosphatases that act on microtubule-associated protein tau protein phosphatases (K. Iqbal, *Ann N Y Acad Sci* 777:132–8 (1996)), modulators of APP proteolytic enzymes and apoE activity (P. T. Lansbury Jr, *Arzneimittedforschung* 45:432–4 (1995)), inhibitors of polysaccharides, such as glycosarninoglycan and proteoglycans, (B. Leveugle et al., *Neuroreport* 5:1389–92 (1994)) and the like. The additional active ingredients may be conjugated to the branched polycation or may be contained separately within a formulation.

The formulations of the invention have the advantage that they are non-toxic in tested forms of administration. For example, parenteral administration of a solution of the formulations of the invention is preferably nontoxic at a dosage of 0.1 mg/mouse, which is an $LD_{50}$ of less than one at 40 mg/Kg.

Administration

Administration of a compound of the invention may be accomplished by any convenient means, including parenteral injection, and direct intracerebral injection or continuous (e.g., long-term or chronic) infusion. The compounds of this invention can be incorporated into a variety of formulations for therapeutic administration. More particularly, the compounds of the present invention can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intratracheal, etc., administration. The active agent may be systemic after administration or may be localized by the use of regional administration, intramural administration, or use of an implant that acts to retain the active dose at the site of implantation.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing sensitizer is placed in proximity to the site of protein deposits (e.g., the site of formation of amyloid deposits associated with neurodegenerative disorders), so that the local concentration of active agent is increased at that site relative to the rest of the body.

The formulations can also be administered by infusion into the brain, and may be administered in either a continuous (e.g., sustained) or non-continuous fashion. Methods, formulations, and devices suitable for delivery to the brain in a continuous (e.g., chronic) or non-continuous (e.g., single, discrete dose per administration) fashion are described in, for example, U.S. Pat. Nos. 5,711,316; 5,832,932; 5,814,014; 5,782,798; 5,752,515; 5,735,814; 5,713,923; 5,686,416; 5,624,898; 5,624,894; 5,124,146; and 4,866,042 (delivery of genetic material).

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosage

Depending on the patient and condition being treated and on the administration route, the compounds of the invention will generally be administered in dosages of 0.001 mg to 5 mg/kg body weight per day. The range is broad, since in general the efficacy of a therapeutic effect for different mammals varies widely with doses typically being 20, 30 or even 40 times smaller (per unit body weight) in man than in animal models (e.g., in the transgenic mice described herein). Similarly the mode of administration can have a large effect on dosage. Thus for example oral dosages in the mouse may be ten times the injection dose. Still higher doses may be used for localized routes of delivery.

A typical dosage may be: a solution suitable for intravenous administration; a tablet taken from two to six times daily; or a one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLE 1

Transfection of PrP$^{Sc}$ Expressing Cells with Dendrimer Compounds

Cells of neuronal origin expressing PrP$^{Sc}$ were examined for the ability of compounds to suppress PrP$^{Sc}$ formation.

Transfection Studies

Stock cultures of N2a and ScN2a cells were maintained in MEM with 10% FBS, 10% Glutamax (Gibco BRL), 100 U penicillin, and 100 µg/ml streptomycin. Cells from a single confluent 100 mm dish were trypsinized and split into 10 separate 60 mm dishes containing DME plus 10% FBS, 10% Glutamax, 100 U penicillin, and 100 µg/ml streptomycin (supplemented DME) one day prior to transfection. Immediately prior to transfection, the dishes were washed twice with 4 ml supplemented DME media and then drained.

For DOTAP-mediated transfection, 15 µg pSPOX MHM2 was resuspended in 150 µl sterile Hepes Buffered Saline (HBS) on the day of transfection. The DNA solution was then mixed with an equal volume of 333 µg/ml DOTAP (Boehringer Mannheim) in HBS in Falcon 2059 tubes and incubated at room temperature for 10 minutes to allow formation of DNA/lipid complexes. Supplemented DME (2.5 ml) was added to the mixture, and this was then pipetted onto drained cell monolayers. The following day, the medium containing DNA/lipid was removed and replaced with fresh supplemented DME. Cells were harvested three days later.

For Superfect™-mediated transfections/exposures, Superfect™ with or without DNA was added to 1 ml supplemented DME in a Falcon 2059 tube to achieve the specific concentrations needed for each experiment. This mixture was pipetted up and down twice and then onto drained cell monolayers. After exposure for the indicated times, the medium containing Superfect™ was removed and replaced with fresh supplemented DME. Cells were harvested at specified times after removal of Superfect™.

Exposures to PPI (DAB-Am-8, Polypropylenimine octaamine Dendrimer, Generation 2.0 Aldrich 46,072-9), Intact PAMAM (Starburst (PAMAM)Dendrimer, Generation 4. Aldrich 41,244-9), PEI (Sigma), poly-(L)lysine (Sigma), and poly-(D) lysine (Sigma) were performed as described above for Superfect™.

Isolation of Protein from Treated Cells

Cells were harvested by lysis in 1.2 ml of 20 mM Tris pH 8.0 containing 100 mM NaCl, 0.5% NP-40, and 0.5% sodium deoxycholate. Nuclei were removed from the lysate by centrifugation at 2000 rpm for 5 min. This lysate typically had a protein concentration of 0.5 mg/ml measured by the BCA assay. For samples not treated with proteinase K, 40 µl of whole lysate (representing 20 µg total protein) was mixed with 40 µl of 2×SDS sample buffer. For proteinase K digestion, 1 ml of lysate was incubated with 20 µg/ml proteinase K (total protein:enzyme ratio=25:1) for 1 hr at 37° C. Proteolytic digestion was terminated by the addition of 8 µl of 0.5M PMSF in absolute ethanol. Samples were then centrifuged for 75 min in a Beckman TLA-45 rotor at 100,000×g at 4° C. The pellet was resuspended by repeated pipetting in 80 µl of 1×SDS sample buffer. The entire sample (representing 0.5 mg total protein before digestion) was loaded for SDS-PAGE.

Western Blot Anaysis

Immunoreactive PrP bands from the DOTAP-mediated transfection were detected before and after digestion with proteinase K with monoclonal antibody 3F4. The construct used to express PrP$^{Sc}$ in the ScN2a cells is MHM2 a chimeric construct that differs from wild-type (wt) MoPrP at positions 108 and 111 (Scott et al., (1992) *Protein Sci.* 1:986–997). Substitution at these positions with the corresponding residues (109 and 112 respectively) from the Syrian hamster (SHa) PrP sequence creates an epitope for 3F4 (Kascsak et al., (1987) *J. Virol.* 61:3688–3693), which does not recognize endogenous wt MoPrP in ScN2a cells and hence facilitates specific detection of the transgene by Western blot.

Following electrophoresis, Western blotting was performed as previously described (Scott et al., (1989) *Cell* 59:847–857). Samples were boiled for 5 minutes and cleared by centrifugation for 1 minute at 14,000 rpm in a Beckman ultrafuge. SDS-PAGE was carried out in 1.5 mm, 12% polyacrylamide gels (Laemmli (1970) *Nature* 227:661–665). Membranes were blocked with 5% nonfat milk protein in PBST (calcium- and magnesium-free PBS plus 0.1% Tween 20) for 1 hour at room temperature. Blocked membranes were incubated with primary R073 polyclonal or 3F4 monoclonal antibody at a 1:5000 dilution in PBST overnight at 4° C.

Following incubation with primary antibody, membranes were washed 3×10 minutes in PBST, incubated with horseradish peroxidase-labeled secondary antibody (Amersham Life Sciences) diluted 1:5000 in PBST for 25 minutes at room temperature and washed again for 3×10 minutes in PBST. After chemiluminescent development with ECL reagent (Amersham) for 1 minute, blots were sealed in plastic covers and exposed to ECL Hypermax film (Amersham). Films were processed automatically in a Konica film processor.

In contrast to DOTAP-transfected cells, ScN2a cells transfected with varying concentrations of Superfect™ and DNA did not appear to contain protease-resistant MHM2. Close scrutiny revealed that, prior to protease digestion, Superfect™-transfected samples express MHM2 bands which are not seen in the background pattern of the control sample. These observations indicate that MHM2 PrP was successfully expressed using Superfect™ transfection reagent, but conversion of M PrP$^C$ to protease-resistant M PrP$^{Sc}$ was inhibited by Superfect™.

To examine whether Superfect™ had affected levels of preexisting PrP$^{Sc}$ in ScN2a cells, the Western blot probed with 3F4 antibody was reprobed with polyclonal antibody R073, which is able to recognize endogenous MoPrP. Remarkably, Superfect™ caused the disappearance of preexisting MoPrP$^{Sc}$ from ScN2a cells in a dose-dependent manner. After treatment with Superfect™, PrP$^{Sc}$ could not be detected in the nuclear fraction, pellet, supernatant, or media. The concentration of Superfect™ required to fully remove preexisting PrP$^{Sc}$ with a three hour exposure was 300 μg/ml, whereas 30 μg/ml was sufficient to interfere with the formation of new MH12 PrP$^{Sc}$ within the same time frame.

Length of exposure dramatically influenced the ability of Superfect™ to remove PrP$^{Sc}$ from ScN2a cells. Whereas a 3 hour exposure to 150 μg/ml Superfect™ significantly lowered PrP$^{Sc}$ levels in ScN2a cells, exposure for 10 min to the same dose of Superfect™ did not affect PrP$^{Sc}$ levels. When ScN2a cells were exposed to 2 μg/ml Superfect™ continuously for 1 week, PrP$^{Sc}$ disappeared completely.

The conditions tested did not appear to be toxic for the cells. Neither 150 μg/ml Superfect™ for 3 hrs nor 2 μg/mil Superfect™ continuously for 1 week caused any obvious changes in cell morphology, viability, or growth as judged by phase contrast microscopy.

EXAMPLE 2

Elimination of PrP$^{Sc}$ by Repeated Exposures to Superfect™

The duration in the reduction in PrP$^{Sc}$ levels after exposure to Superfect™ was examined, and it was shown that this reduction could persist for extended periods after removal of Superfect™. Following the exposure of ScN2a cells to a single dose of 150 μg/ml Superfect™ for 3 hrs, PrP$^{Sc}$ levels remained low for one week, but returned to near baseline levels after 3 weeks in culture without Superfect™.

In contrast, when ScN2a cells were exposed to 4 separate doses of Superfect™ over the course of 16 days, very little PrP$^{Sc}$ could be detected 4 weeks after the final exposure to Superfect™. This result offers hope that prolonged exposure to Superfect™ may lead to long term cure of scrapie infection in cultured cells.

EXAMPLE 3

Superfect™ does not Destroy PrP$^{Sc}$ Directly

The dendrimer Superfect™ was used to determine if it could exert a similar inhibitory effect on PrP$^{Sc}$ in either crude brain homogenates or purified PrP 27–30 rods. Brain homogenates from normal and scrapie-affected Syrian hamsters (10% (w/v) in sterile PBS) were prepared by repeated extrusion through syringe needles of successively smaller size, from 18 to 22 gauge. Nuclei and debris were removed by centrifugation at 1000×g for 10 min. The bicinchnoninic acid (BCA) protein assay (Pierce) was used to determine protein concentration. Homogenates were adjusted to 10 mg/ml protein with PBS and 50 μl was added to 450 μl of lysis buffer containing 100 mM NaCl, 1 mM EDTA, 0.55% sodium deoxycholate, 0.55% Triton X-100, and 50 mM Tris-HCl pH 7.5. This mixture was then incubated with 0–300 μg/ml Superfect™ for 3 hrs at 37° C. and then centrifuged for 10 min at 14,000 rpm in a Beckman Ultrafuge. The pellet was resuspended in 450 μl lysis buffer without Superfect™. Proteinase K (Boehringer Mannheim) was added to achieve a final concentration of 20 μg/ml, and thus the ratio of total protein/enzyme was 50:1. Samples were incubated for 1 h at 37° C. Proteolytic digestion was terminated by the addition of 8 μl of 0.5 M PMSF in ethanol. Samples were then centrifuged for 75 min in a Beckman TLA-45 rotor at 100,000×g at 4° C. Undigested samples (10 μl) were mixed with an equal volume of 2×SDS sample buffer. For digested samples, the pellet was resuspended by repeated pipetting in 100 μl 1×SDS sample buffer. Twenty μl (equivalent to 100 μg of total protein prior to proteinase K digestion) of each sample was loaded for SDS-PAGE.

PrP 27–30 rods were purified from scrapie-affected Syrian hamster brains and previously described (Prusiner et al., (1983) Cell 35:349–358). Purified rods (3.5 μg/ml) were incubated with or without 900 μg/ml Superfect™ in 100 μl supplemented DME. After 16 hrs at 37° C., the suspension was centrifuged at 100,000×g at 4° C. The pellet was resuspended in 500 μl of buffer containing 1 mg/ml BSA, 100 mM NaCl, 1 mM EDTA, 0.55% sodium deoxycholate, 0.55% Triton X-100, and 50 mM Tris-HCl pH 7.5. proteinase K was added to achieve a final concentration of 20 μg/ml. Samples were incubated for 1 h at 37° C. Proteolytic digestion was terminated by the addition of 8 μl of 0.5 M Pefabloc (Boehringer Mannheim). Samples were then centrifuged for 75 min at 100,000×g at 4° C. Undigested samples (50 μl) were mixed with an equal volume of 2×SDS sample buffer. For digested samples, the pellet was resuspended by repeated pipetting in 100 μl 1×SDS sample buffer. Forty μl of each sample was loaded for SDS-PAGE.

When Superfect™ was mixed with either crude homogenates of scrapie-affected Syrian hamsters or with purified Syrian hamster PrP 27–30, there was no significant change in the level of proteinase K-resistant PrP$^{Sc}$. These results suggest that the removal of PrP$^{Sc}$ from ScN2a cells by SuperfectTm depends on the presence of intact cellular machinery.

EXAMPLE 4

Clearance of PrP$^{Sc}$ Levels by Other Dendritic Polycations

The Superfectrm compound is a high molecular weight component of heat-degraded PAMAM Starburst dendrimers, which is a cationic, highly-branched, monodisperse polymers (Tang et al., (1996) Bioconjugate Chem. 7:703–714). To identify other potentially useful anti-prion therapeutic agents, we screened three other dendritic polycations and two linear cationic polymers for their ability to clear PrP$^{Sc}$ from ScN2a cells. Among the dendritic macromolecules tested, polyetheleneimine (PEI) was the most potent, removing the majority of PrP$^{Sc}$ from ScN2a cells after 3 hrs when used at a concentration of 10 μg/ml. Intact PAMAM displayed a potency comparable to Superfect™, removing approximately half of the detectable PrP$^{Sc}$ when used at a concentration of 50 μg/ml. In contrast, the dendrimer polypropyleneimine (PPI), poly-(L)lysine, and the linear polycation poly-(D)lysine failed to reduce PrPSc levels at concentrations between 10–50 μg/ml. These results demonstrate that a branched polymeric architecture is required to clear PrP$^{Sc}$. Furthermore, exposure of ScN2a cells to either PEI or intact PAMAM for one week at a concentration of 1.5 μg/ml completely removes PrP$^{Sc}$, effectively curing the cells of scrapie infection.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A pharmaceutical composition for the treatment of PrP$^{Sc}$ formation in an animal, said composition comprising:
   an unconjugated dendritic polycation in an amount effective to decrease levels of PrP$^{Sc}$ in the subject; and
   a pharmaceutically acceptable excipient.

2. The pharmaceutical composition of claim 1, wherein one branching unit of the dendritic polycation is positively charged.

3. The pharmaceutical composition of claim 2, wherein the dendritic polycation is comprised of a plurality of charged branching units.

4. The pharmaceutical composition of claim 3, wherein the dendritic polycation is comprised of a plurality of branching units having the same chemical structure.

5. The pharmaceutical composition of claim 3, wherein the dendritic polycation is selected from the group consisting of polypropylene imine, polyethyleneimine (PEI) poly(4'-aza-4'-methylheptamethylene D-glucaramide), and polyamidoamines.

6. The pharmaceutical composition of claim 1, further comprising an effective amount of a second therapeutic agent selected from the group consisting of: an analgesic agent, an antimicrobial agent, anti-inflammatory agent, an antioncogenic agent, and an antiviral agent wherein the second therapeutic agent is not conjugated to the dendritic polycation.

7. A method of enhancing clearance of $PrP^{Sc}$ from cells, comprising the steps of:

contacting cells with an unconjugated dendritic polycation; and allowing the dendritic polycation to remain in contact with the cells for a time sufficient to enhance the rate of clearance of $PrP^{Sc}$ from the cells.

8. The method of claim 7, wherein said dendritic polycation is repeatedly brought into contact with the cells.

9. The method of claim 7, Wherein one branching unit of the polycation is positively charged.

10. The method of claim 9, wherein the dendritic polycation is comprised of a plurality of charged branching units.

11. The method of claim 10, wherein the dendritic polycation is selected from the group consisting of polypropylene imine, polyethyleneimine (PEI) poly(4'-aza-4'-methylheptamethylene D-glucaramide), polyamidoamines and variants or fragments thereof.

12. The method of claim 7, wherein the cells are cells of brain tissue of a human.

13. The method of claim 7, herein the dendritic polycation is administered to a subject in an amount non-toxic to the subject at a dosage of 0.001 mg to 1 mg/kg body weight per day.

14. The method of claim 7, wherein the cells are within an animal selected from the group consisting of a human, cow, sheep, deer, dog, cat, goat, chicken and turkey.

* * * * *

UNITED STATES PATENT AND TRADEMARK OFFICE
CERTIFICATE OF CORRECTION

PATENT NO. : 6,214,366 B1
DATED : April 10, 2001
INVENTOR(S) : Stanley B. Prusiner; Surachai Supattapone; Michael Scott It is certified that error appears in the above-identified patent and that said Letters Patent is hereby corrected as shown below:

<u>Claim 13,</u>
Line 1, change "herein" to -- wherein --

Signed and Sealed this

Twenty-eighth Day of August, 2001

*Attest:*

NICHOLAS P. GODICI
*Attesting Officer*     *Acting Director of the United States Patent and Trademark Office*